US006397103B1

(12) United States Patent
Canali

(10) Patent No.: US 6,397,103 B1
(45) Date of Patent: May 28, 2002

(54) APPARATUS FOR THE EMISSION OF A COMBINED FLOW OF ELECTRONS AND ELECTROMAGNETIC RADIATIONS

(76) Inventor: Angelo Canali, Parma Borgo della Posta n.12, Parma (IT)

( * ) Notice: Subject to any disclaimer, the term of this patent is extended or adjusted under 35 U.S.C. 154(b) by 0 days.

(21) Appl. No.: 09/455,131

(22) Filed: Dec. 6, 1999

Related U.S. Application Data

(63) Continuation-in-part of application No. 08/573,886, filed on Dec. 18, 1995, now abandoned.

(30) Foreign Application Priority Data

Dec. 27, 1994 (IT) ........................................ MI94A2653

(51) Int. Cl.[7] .................................................. A61N 1/18

(52) U.S. Cl. ............................... 607/2; 607/75; 607/50

(58) Field of Search .......................... 607/2, 46.48, 50, 607/75, 115

*Primary Examiner*—Jeffrey R. Jastrzab

(57) ABSTRACT

Apparatus for the emission of a combined flow of electrons and electromagnetic radiations comprising two electrical circuits (2,2') having opposite polarities: positive (+) and negative (–). Each circuit (2,2') comprises an electrical or electronic device (7,7') suitable to supply a direct current whose voltage is comprised between 4,000 and 80,000 V, and whose intensity is comprised between 0.05 and 0.5 mA, and a plate-like conductor (9,9') provided with one or more bundles of carbon fibers which act as a pointed conductors, which terminal is connected to the outlet (8,8') of said electrical or electronic device. When the two plates (9,9') provided with bundles of carbon fibers (11,11'), are positioned and approached one in front of the other, a combined flow of electrons and electromagnetic waves circulating from pole (–) to pole (+) is obtained.

13 Claims, 3 Drawing Sheets

APPARATUS FOR THE EMISSION OF A COMBINED FLOW OF ELECTRONS AND ELECTROMAGNETIC RADIATIONS

This application is a continuation-in-part application of U.S. patent application Ser. No. 08/573,886 filed on Dec. 18, 1995 now abandoned.

BACKGROUND OF THE INVENTION

1. Field of the Invention

This invention relates to an apparatus for the emission of a combined flow of electrons and electromagnetic radiations. The apparatus of this invention has a specific application in the medical sector for the therapeutic treatment for activating, regenerating and revitalizing living cells and in particular human cells.

2. Description of the Prior Art

It is known that when a continuous flow of electrons is directed against a human body, a current forms which passes, more or less completely, through the body, according to a complicated exchange operation between the atoms that make up the cells, causing in this way an energy exchange between the cells and the generation in their inside of electrochemical phenomena such as to create oxygenation and revitalization conditions.

It is also known that, because of their structure, living cells are animated by vibrations produced by the continuous action of external electromagnetic radiations (cosmic rays). When a cell, thanks to the conformation of its nucleus, and in particular to the precise length and structure of its filament, which is different from cell to cell, even of the same type, is excited by a vibratory action produced by the electromagnetic radiations, it starts vibrating and resonating with its own specific frequency.

Namely, as a consequence of its shape and the size of its filament, each cell vibrates according to its own wavelength.

It ensues from this that all the cells that form an organ, or a body as a whole, vibrate according to different wavelengths, even though their magnitude order differs only to a minimum extent and comprises rather limited frequency bands.

The cells, following lasting intensity variations of the above external electromagnetic radiations, undergo vibratory alterations and modifications of the intracellular energy system, and consequently they lose their original oscillatory capacities.

Due to this effect, the cells lose their functional capacity, reducing the intensity and the coordination of the metabolic processes. The cells that are in such state are usually called "depressed cells".

However, based on studies and researches carried out on said cell behaviour, it is possible to regenerate the "depressed"cells by exciting them with a flow of large spectrum artificial electromagnetic radiations, such as to comprise the frequencies of all the cells of the human body.

With reference to humans, it can be assumed that many of the conditions of psycophysical imbalance, such as asthenia, fatigue, depression, etc., may arise from imbalances of the cellular bioelectric system, caused either by the variations of the electromagnetic intensity which humans are usually submitted to in their environment, or by oxygenation deficit in the inside of the cells.

It is known that said functional anomalies of the human cells can be overcome by means of a treatment with a combined flow of electrons and electromagnetic radiations, as living cells are characterized in that they always tend to resyntonize on their original resonance.

Electrical medical instruments for increasing the metabolic activity of desired cells by inducing electrical current flow through the cells to be treated are known. The known instruments comprise a source of direct electrical energy, a pair of output terminals connected to a pair of electrodes which are adapted to be placed in contact with healty tissue opposite one another across damaged tissue, and means for generating from the energy source a voltage wave and impressing it across the output terminals.

Static or variable electrical fields for prophylactic and therapeutic purposes are also used, for example in the application to the leg of a patient.

Apparatuses are also known that allow to emit combined electrons and electromagnetic currents, utilizable for the aforementioned treatment. Such apparatuses comprise basically an electrical circuit formed by an electrical or electrons device, such as for instance, a transformer which, fed by alternated current from the mains, can supply at the outlet a positive or negative direct current of high voltage and very low intensity, which is conveyed to a conductor with pointed ends. Such pointed ends are directed towards the concerned part of the body which is therefore swept over by the bundles of electrons and electromagnetic radiations coming from said points.

However, these apparatuses have some drawbacks which reduce their effectiveness, as will be precised in the following. A first serious drawback ensues from the fact that, as the direct current available from the transformer has only one polarity, negative or positive, the radiation flow emitted by the partly pointed ends of the conductor, disperses, tending to circulate at the epidermic level and groundwards, flowing in this way outside the body part instead of penetrating in depth, as the system formed by the pointed ends of the conductor and the patient's body has a certain electrical resistivity.

A further serious drawback is due to the fact that the pointed ends of the conductor allow to have rather limited radiation flow capacities and therefore such apparatuses provide very low performances.

SUMMARY OF THE INVENTION

In its more general aspects, the present invention allows to overcome the above drawback of the prior art by providing an apparatus which comprises two electrical circuits, provided each with an electrical or electronic device, such as for instance a transformer with rectifying diodes, capable of providing at the outlet a direct current of polarity opposite from one another, high voltage ranging from 4,000 to 80,000 V and very low intensity ranging from 0.05 to 0.5 mA.

The electrical or electronic devices of the two electrical circuits supply direct currents of opposite polarity, one positive (+) and one negative (–), to two plate-like conductors equipped with at least one bundle of carbon fibres which act as pointed ends.

The subject matter of the present invention is, therefore, an apparatus for the emission of a combined flow of electrons and electromagnetic radiations fed by an alternating current distribution, comprising two electrical circuits having opposite polarity, one circuit having a positive polarity (+) and the other circuit having a negative polarity (–), each electrical circuit comprising an electrical or electronic device transforming the alternating current into direct current and delivering a direct current having a voltage comprised between 4,000 and 80,000 V and an intensity comprised between 0.05 and 0.5 mA, and a plate-like end conductor connected to each outlet of said electrical or electronic device and provided with at least one bundle of pointed conductors.

The at least one bundle of pointed conductors may be up to 100 and each bundle comprises from 50 to 10,000 of pointed conductors.

The pointed conductors may be carbon fibres. Any type of carbon fibres can be used in the apparatus of the present invention; they are composed of at least 90% carbon and are commonly produced by carbonizing organic polymers in filamentary form, such as, for example, acrylic fibres.

The apparatus of this invention allows to realize a combined flow of electrons and of electromagnetic radiations, said flow being all the more consistent and better distributed the higher is the number of bundles provided.

The arrangement of the plates with the carbon fibre bundles one in front of the other allows to obtain a strong circulation of combined radiations from plate (−) to plate (+). If a part or the whole body of a patient, kept insulated from the ground, is interposed between said plates, said radiations pass through him, reaching also the innermost organs.

BRIEF DESCRIPTION OF THE DRAWING

The characteristics of the apparatus of this invention will be better understood from the following detailed description.

DESCRIPTION OF THE PREFERRED EMBODIMENT

Figure 1:
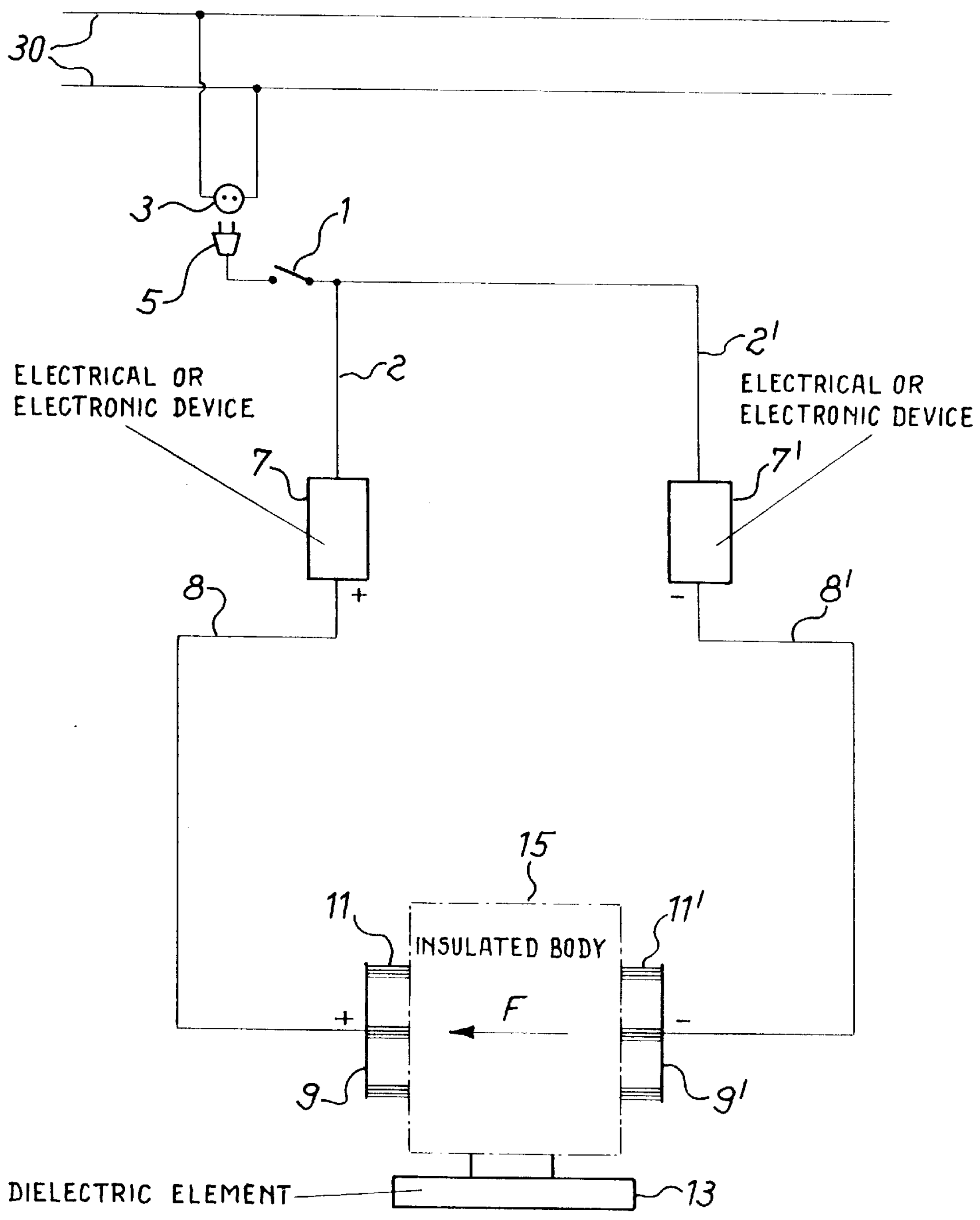
FIG. 1 shows the electric schema of a preferred embodiment, supplied by ways of non limitative example, of the apparatus of the present invention.
Figure 2:
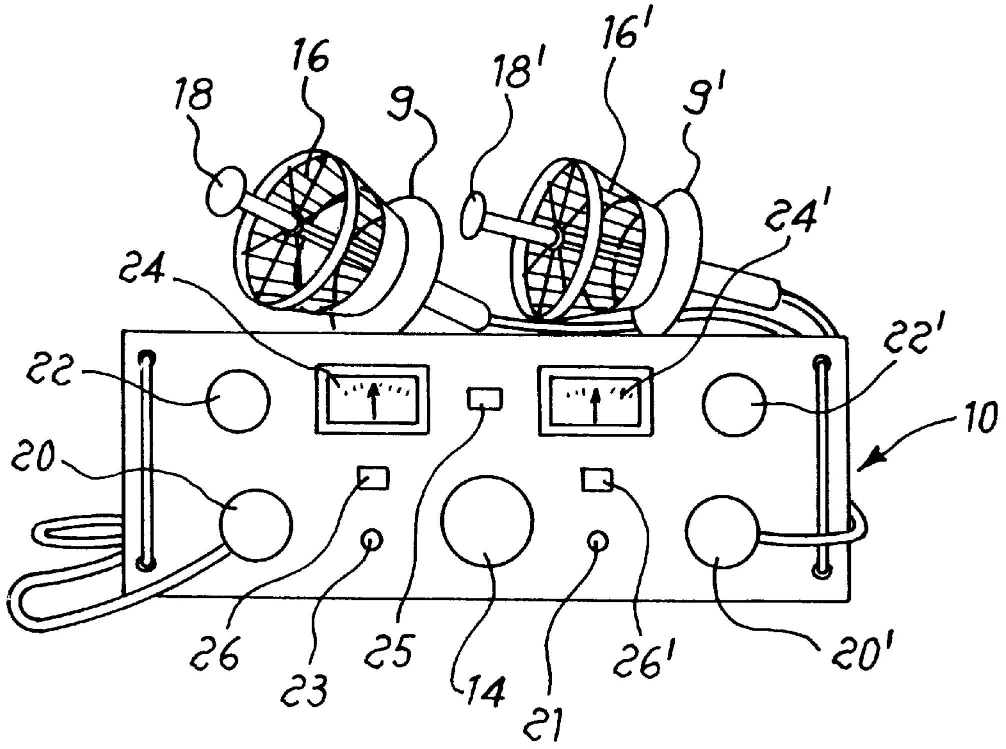
FIG. 2 shows a front view of the apparatus of the present invention, particularly useful for arterial and venous vascular diseases, including the electric schema of FIG. 1.
Figure 5:
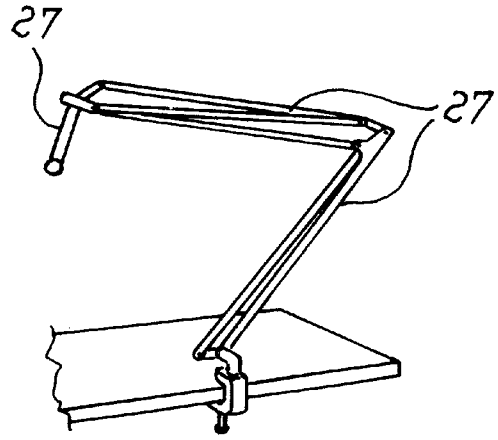
FIGS. 5 and 6 illustrate the articulated or flexible arms for supporting an end conductor; without and with the end conductor, respectively.
Figure 6:
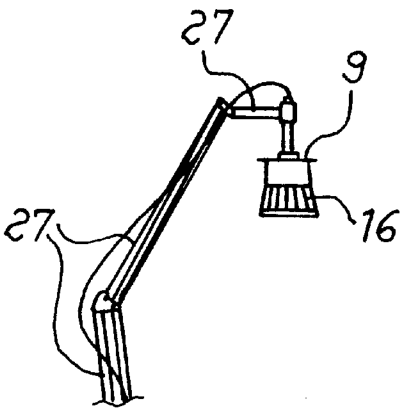
Figure 3:
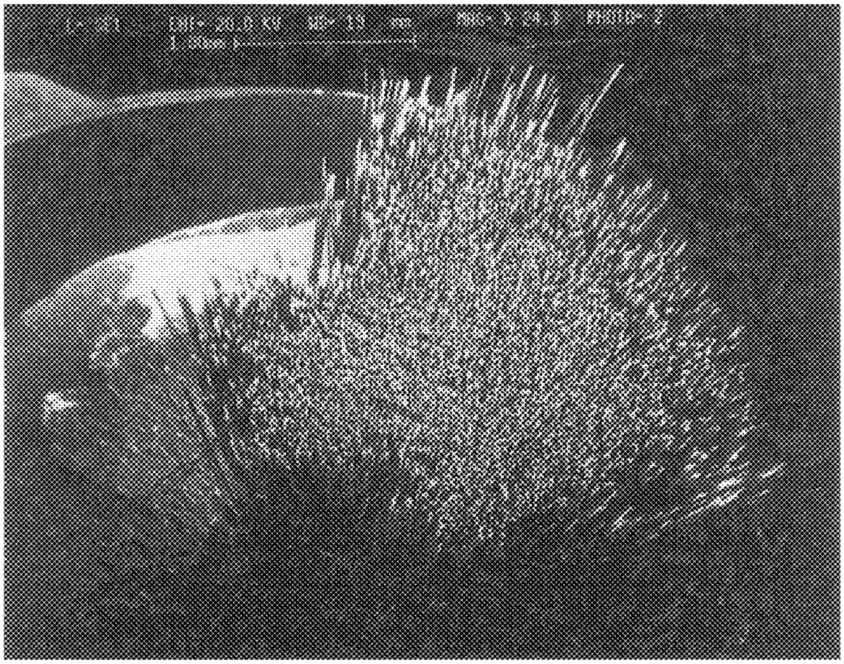
FIG. 3 shows a bundle of carbon fibres obtained by a scanning electron microscope at × 24.3 magnification.
Figure 4:
FIG. 4 shows the carbon fibres of FIG. 3 obtained by a scanning electron microscope at × 321 magnification.

With reference to the aforementioned FIG. 1, the apparatus (10) of this invention includes the electric schema illustrated in FIG. 1, which comprises two electrical circuits (2,2'), fed by a same network of alternated current 30 (for instance, 220 V a.c.) through a tap (3), a plug (5) and a switch (1).

Each electrical circuit (2,2') comprises an electrical or electronic device (7,7'), such as for instance a transformer with rectifying diodes, which can supply each at the outlet (8,8') a direct current of opposite polarity relatively to one another, high voltage and very low intensity.

In particular, said electrical or electronic devices supply at the outlets (8,8') direct currents with a voltage of 4,000–80,000 V and an intensity of 0.05–0.5 mA, one of which has a (+) polarity in device (7) and the other one (−) a polarity in device (7').

The above outlets (8,8') are respectively connected to two plate-like conductors (9,9'). Each plate (9,9') is provided with at least one carbon fibre bundle (11,11') (three in FIG. 1), which act as pointed conductors. When these plate-like conductors (9,9')are positioned and approached one in face of the other, a circulation of electrons and electromagnetic radiations is obtained in the direction of arrow F from pole (−) to pole (+). If a part of a body (15) (or the whole body), insulated from the ground by means of a dielectric element (13), is placed between said plate-like conductors (9,9'), said part is passed through by said radiations, effecting in this way all the cells that are present along the path of said radiations, even in depth, which cells, as a consequence, are regenerated and revitalized.

The plate-like conductors (9,9') are made of conductive materials, such as copper, aluminium, etc. and the carbon fibres bundles (11,11') are fixed to said plate-like conductors. The fixing of the carbon fibres to the plate-like conductor may be obtained by any known fixing means ensuring the electrical connection between the conductive plate-like conductor (9,9') and each carbon fibre of each bundle (11,11').

The plate-like conductors (9,9') may have any shape, such as square, rectangular, triangular, polygonal, or circular. The surface of the plate-like conductors (9,9') is not critical and depends on the surface of the body to be submitted to the radiations.

Each plate-like conductor (9,9') with the bundles (11,11') of carbon fibres fixed thereto may be protected by a disposable bandage (16,16') of non-conductive insulating material. The bandage (16,16') is preferably glass-shaped with the bundles (11,11') fixed to the bottom. The lateral wall of the bandage (16,16') may be slotted and provided with a cross support at its free end.

A disposable spacer (18,18') may be connected to the cross-support of each bandage (16,16') such as by groove-and-tongue joint.

The disposable bandage (16,16') and the spacer (18,18') preferably are made of plastic material.

The bandage (16,16') protects the carbon fibres from the contact with the patient or the operator during the use of the apparatus. The spacer (18,18') assures that the conductor (9,9') or the carbon fibres are not in contact with the skin.

The plate-like conductors (9,9') are connected to the apparatus (10) by a connecting cables (20,20') with stream output.

The apparatus (10) may be provided with a first outlet (21) for a cable with cuff for connection to operator; a second outlet (23) for a cable to be connected to a disposable cuff for connecting the patient and, for each plate-like conductor (9,9'), with an intensity regulator (22,22') and an Ampere meter (24,24')for determining the $\mu$ A value of the current applied. A warning light (25) to control when the apparatus is in use and starter buttons (26,26') may be provided.

The treatment time may be predetermined and regulated by a timer (14).

The arrangement of the plate-like conductors (9,9') with the carbon fibre bundles fixed thereto one in front of the other allows to obtain a strong circulation of combined flow of electrons and electromagnetic radiations from plate (−) to plate (+).

The number of carbon fibre bundles (11,11') on each plate-like conductor (9,9') may range from 1 to 100 and more, depending on the surface of the plate-like conductor (9,9'). Each carbon fibre bundle (11,11') may have a surface of its cross-section comprised between 0.001 and 10 $mm^2$, preferably between 0.1 and 2 $mm^2$, and is formed by a number of carbon fibres comprised between 50 and 10,000.

The dielectric element (13) may be a chair, an arm-chair or a bed with feet from insulating plastic material. The plate-like conductors (9,9') with the carbon fibre bundles (11,11') have generally the shape of brushes, supported by articulated or flexible arms (27), to make their application to the various parts of the human body easier, placing them near the body and not in touch with the same; the spaces (18,18') assure to avoid the contact between the end conductors (9,9') and the treated parts of the human body.

The use of carbon fibres allows also to eliminate and to prevent possible electrostatic shocks.

The apparatus of this invention is characterized by the absence of harmful stimulations and by a complete analgesia, as it activates the cellular bioelectric system without contraindications, independently on the clinical conditions of the patient when he is submitted to the action of the apparatus. The cells that at the time of the application of the radiations are already in balanced conditions, i.e. not "depressed", are not electrically modified, but remain in their ideal balanced conditions.

The apparatus of the present invention has been utilized in the field of vascular disease for the treatment of bed sores, cicatrisation deficiencies and skin and venous ulcers and has been successful in more than 80% of the cases.

In particular, in the treatment of deep ulcerating of the skin with sanious edges, severe hyperaemia and dyschromia, after 20 treatment sessions, a visible reduction of the ulcerated area has been noticed, both in depth and on the surface, with regression of the phlogistic phenomena of the hyperaemia and of the dyschromia of the skin. After 40 treatment sessions, the area has returned completely to normal with re-epithelialisation and normochromia of the necrotic area.

Even in the most serious and advanced cases from the necrobiotic point of view, regeneration and return to full integrity has been obtained at a very high percentage (80% and over) of cases. In every case treated, even in the remaining 20% or less, a considerable improvement has in any case been achieved as far as concerns regression of local pain and of the concurrent phlogistic complications.

Even after the first applications it has been possible to note appreciable effects with considerable and concrete benefits for the patient. The noted effects have been: slowdown and final ceasing of the exudation and phlogistic phenomena; early appearance of granulation tissue; marked increase of the blood flow with regression of the oedema and of peri-lesional cyanosis in the area treated; rapid cicatrisation and stable healing in time.

The apparatus of the present invention was used in the treatment of ulcers. 116 patients were treated, that is 32 patients suffering from venous insufficiency leg ulcers, 70 patients suffering from pressure ulcers and 14 patients suffering from diabetic ulcers.

The results shown the effectiveness of the ionic flux current therapy in enhancing the healing rate of the chronic ulcers that have been unresponsive to conventional therapies.

The most dramatic clinical difference between ionic flux current therapy and conventional treatment schedules resulted in the immediate pain decrease with persistent pain relief.

The apparatus of the present invention has been used even in the sport derived traumathology as a means of generation to injured athletes.

The treatment has been carried out on 381 patients: 230 males and 151 females having an age comprised between 12 to 62 years. The patients showed the following pathologic diseases:

simple cutaneous injuries;

contusions;

muscular traumas: with intertissular hemorrhage and intramuscular bleeding;

articular traumas;

tendosynovitis and peritendinitis;

capsule-ligament sprains;

epicondylitis (tennis's elbow) and osteochondrosis and tendinopathies;

myentasis.

The treatment comprised:

Number of applications: 5–15;

Frequency: 1–3 times/day;

Application duration:
- 15 min. for the first week,
- 30 min. for the other weeks;

Intensity:
- low in the first week;
- higher in the other weeks and regulated on the basis of the results The results achieved were:

1) diminution of the suffering as well as reduction of edema when it is still at the first stage;

2) regeneration gets on sooner than that expected so the patients can soon train again as well;

3) 100% of recovery

The treatment of the present invention on 1,228 patients suffering from sport injuries resulted in immediate relief of pain and reduction of edema.

Although the preferred embodiment of this invention has been shown and described, it should be understood that various modifications and variations may be resorted to without departing from the scope of the invention as disclosed and claimed herein.

What is claimed is:

1. An apparatus for the emission of a combined flow of electrons and electromagnetic radiations by a distribution network of alternating current, which apparatus comprises:

a) two electrical circuits (2,2'), said circuits having opposite polarity, one circuit (2) having a positive polarity (+) and the other circuit (2') having a negative polarity (−); each circuit comprising an electrical or electronic device (7, 7'), said devices (7, 7') transforming the alternating current of said distribution network to direct current and delivering direct current;

b) two outlets (8, 8'), one outlet (8) being connected to the circuit (2) which has positive polarity, and the other outlet (8') being connected to the circuit (2') having negative polarity; and c) two plate-like end conductors (9, 9') each of said conductors being provided with at least one bundle (11,11') of pointed conductors, one conductor (9) being connected to the outlet (8) of said circuit (2) which has positive polarity, the other conductor (9') being connected to the outlet (8') of said circuit (2') which has negative polarity.

2. The apparatus according to claim 1, wherein the direct current delivered has a voltage comprised between 4,000 and 80,000 V and an intensity comprised between 0.05 and 0.5 mA.

3. The apparatus according to claim 1, wherein there are up to 100 bundles (11, 11') of pointed conductors.

4. The apparatus according to claim 1, wherein the pointed conductors are carbon fibres.

5. The apparatus according to claim 1, wherein a combined flow of electrons and electromagnetic waves circulating from circuit (2') having negative polarity to circuit (2) having positive polarity is obtained when said plates (9,9') are positioned and approached one in front of the other.

6. The apparatus according to claim 1, wherein said electrical or electronic devices (7, 7') for the transformation of the alternating current of the distribution network into direct current are a transformer with rectifying diodes.

7. The apparatus according to claim 1, wherein the conductors (9,9') are made of a metal which is a member of the group consisting of copper and aluminum.

8. The apparatus according to claim 1, wherein the conductors (9,9') have square, rectangular, triangular, polygonal or circular shape.

9. The apparatus according to claim 1, wherein said conductors (9,9') have a surface and the number of said bundles (11,11') on the surface of each of said conductors depends on said surface.

10. The apparatus according to claim 3, wherein each bundle of carbon fibers (11,11') has a surface with cross-section comprised between 0.001 and 10 $mm^2$ and is formed by a number of carbon fibers comprised between 50 and 10,000.

11. The apparatus according to claim 10, wherein each bundle of carbon fibers (11,11') has a surface with cross-section comprised between 0.1 and 2 $mm^2$.

12. A method for the treatment of bed sores, cicatrisation deficiencies and skin and venous ulcers, which method consists of:

exposing said part of said human body, insulated from the ground, to an apparatus for the emission of a combined flow of electrons and electromagnetic radiations fed by a distribution network of alternating current, which apparatus comprises:

a) two electrical circuits (2,2'), said circuits having opposite polarity, one circuit (2) having a positive polarity (+) and the other circuit (2') having a negative polarity (−); each circuit comprising an electrical or electronic device (7,7'), said devices (7,7') transforming the alternating current of said distribution network into direct current and delivering a direct current;

b) two outlets (8,8'), one outlet (8) being connected to the circuit (2) which has positive polarity, and the other outlet (8') being connected to the circuit (2') having negative polarity; and c) two plate-like end conductors (9,9') each of said conductors being provided with at least one bundle (11,11') of carbon fibers, said carbon fibers bundles acting as pointed conductors, one conductor (9) being connected to the outlet (8) of said circuit (2) which has positive polarity, the other conductor (9') being connected to the outlet (8') of said circuit (2') which has negative polarity, interposing the part of a body to be treated between said two plate-like end conductors (9,9'), and exciting said part with a combined flow of electrons and electromagnetic radiations obtained by delivering between said plate-like conductors (9,9') a direct current having a voltage comprised between 4,000 and 80,000 V and an intensity comprised between 0.05 and 0.5 mA.

13. A method for the treatment of a sport derived traumathology, which method consists of:

exposing the part of the human body, insulated from the ground, to an apparatus for the emission of a combined flow of electrons and electromagnetic radiations fed by a distribution network of alternating current, which apparatus comprises:

a) two electrical circuits (2,2'), said circuits having opposite polarity, one circuit (2) having a positive polarity (+) and the other circuit (2') having a negative polarity (−); each circuit comprising an electrical or electronic device (7,7'), said devices (7,7') transforming the alternating current of said distribution network into direct current and delivering a direct current;

b) two outlets (8,8'), one outlet (8) being connected to the circuit (2) which has positive polarity, and the other outlet (8') being connected to the circuit (2') having negative polarity; and c) two plate-like end conductors (9,9') each of said conductors being provided with at least one bundle (11,11') of carbon fibers, said carbon fibers bundles acting as pointed conductors, one conductor (9) being connected to the outlet (8) of said circuit (2) which has positive polarity, the other conductor (9') being connected to the outlet (8') of said circuit (2') which has negative polarity, interposing the part of the body to be treated between said two plate-like end conductors (9,9'), and exciting said part with a combined flow of electrons and electromagnetic radiations obtained by delivering between said plate-like conductors (9,9') a direct current having a voltage comprised between 4,000 and 80,000 V and an intensity comprised between 0.05 and 0.5 mA.

* * * * *